United States Patent [19]

Seid

[11] 4,273,534
[45] Jun. 16, 1981

[54] AMALGAM CARRIER AND DISPENSER

[75] Inventor: Paul A. Seid, New City, N.Y.

[73] Assignee: Sultan Dental Products, Inc., Englewood, N.J.

[21] Appl. No.: 69,613

[22] Filed: Aug. 27, 1979

[51] Int. Cl.³ .............................................. A61C 5/04
[52] U.S. Cl. ..................................... 433/90; 433/164
[58] Field of Search ...................... 433/83, 89, 90, 164

[56] References Cited

U.S. PATENT DOCUMENTS

| 146,380 | 1/1874 | Chance | 433/164 |
|---|---|---|---|
| 246,981 | 9/1881 | Shumway | 433/164 |
| 363,630 | 5/1887 | Greenlee | 433/83 |
| 608,984 | 8/1898 | Hanson | 433/90 |
| 1,469,004 | 9/1923 | Holtz | 433/90 |
| 1,797,866 | 3/1931 | Ivory | 433/89 |
| 2,903,794 | 9/1959 | Carfagni | 433/90 |

Primary Examiner—G. E. McNeill
Assistant Examiner—John J. Wilson
Attorney, Agent, or Firm—Steinberg & Raskin

[57] ABSTRACT

An amalgam carrier and dispenser constructed in a manner such that its effective life is at least about five times greater than that of conventional instruments. The amalgam carrier and dispenser includes a handle, a plunger element affixed to the handle having a plunger portion, and an open ended sleeve element having an internal bore formed therein in which the plunger portion is slideably located. According to the invention, the plunger portion has a terminal end region, preferably in the form of a tip portion, which is formed of a hard metallic material while the clearance between the plunger portion and the internal sleeve element bore is smaller relative to clearances provided in conventional instruments. By these provisions, the effects of abrasion of the surfaces of the plunger and associated components which would otherwise be caused by the action of the amalgam on these components is significantly reduced relative to conventional instruments. Preferably, the axial length of the terminal end region of the plunger is greater than a predetermined minimum.

13 Claims, 8 Drawing Figures

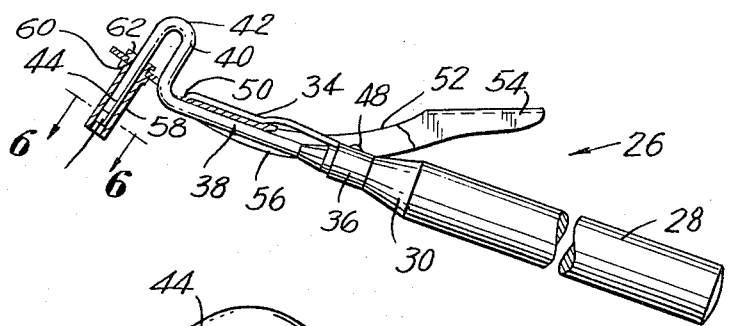
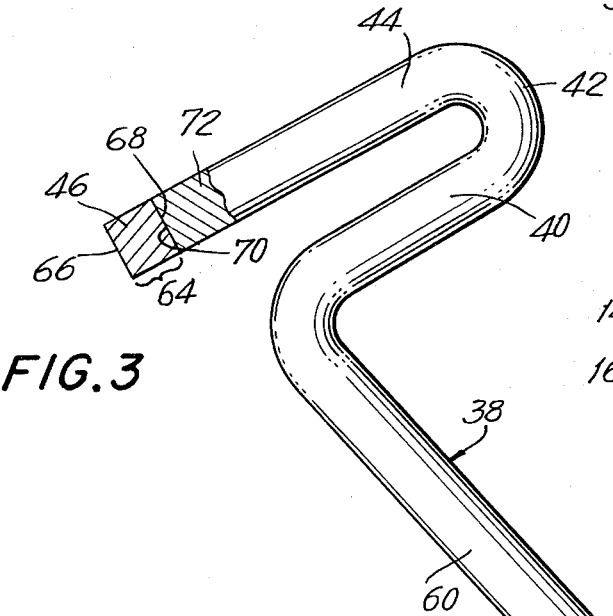
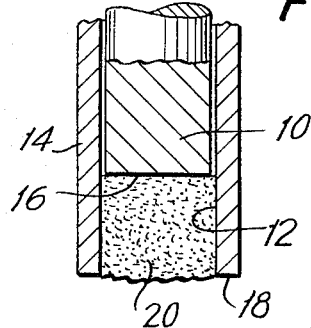
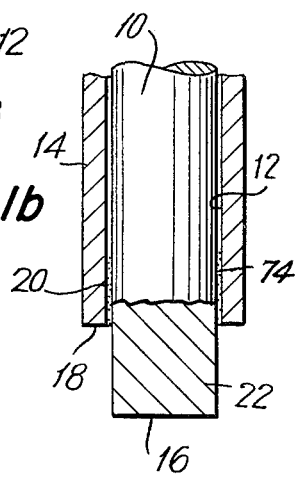
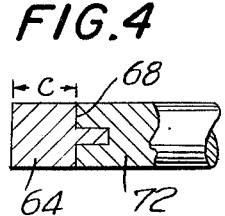
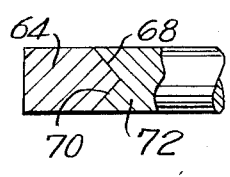
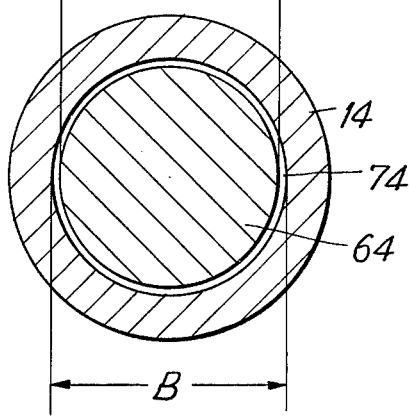
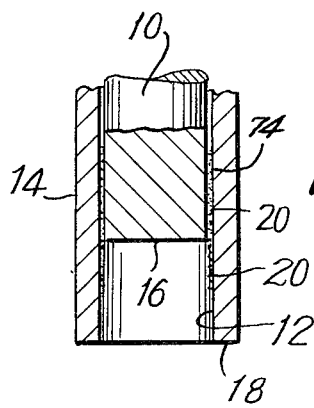

AMALGAM CARRIER AND DISPENSER

BACKGROUND OF THE INVENTION

This invention relates generally to dental instruments and, more particularly, to an instrument for carrying and dispensing dental amalgam for use in connection with depositing the amalgam in tooth cavities.

Amalgam carriers and dispensers have in the past taken many different forms. For example, various dental amalgam carriers and dispensers are illustrated in the following U.S. patents: U.S. Pat. Nos. 1,797,866; U.S. Pat. No. 2,503,156; U.S. Pat. No. 2,679,102; U.S. Pat. No. 3,221,409; U.S. Pat. No. 3,091,860 and U.S. Pat. No. 3,537,617.

Generally, conventional amalgam carriers and dispensers include apparatus wherein a plunger, formed of a metallic material such as stainless steel, is slideably located within the internal bore of a sleeve. The plunger is normally located so that its forward end surface is recessed within the bore so as to define a cavity or space within the sleeve into which the amalgam is condensed or packed. The dentist then locates the instrument such that the amalgam filled sleeve is within the tooth cavity to be treated, the latter having been previously prepared such as by drilling, whereupon appropriate levers are actuated to cause the plunger to move axially within the sleeve bore so that the terminal end region of the plunger extends beyond the open end of the sleeve bore thereby expelling or dispensing the amalgam into the tooth cavity.

Such conventional amalgam carriers and dispensers, however, are not entirely satisfactory. More particular, conventional amalgams, which usually comprise alloys of mercury with one or more of tin, cadmium, silver, and/or copper in cut or spherical particle design are extremely hard materials. Further, in recent years, amalgams have been formulated in a manner such that their hardness has been increased to an even greater extent. Such modern amalgams comprise copper phase, dispersed phase, ternary, spherical and spherical blend alloys in combination with mercury. Due to the hardness of conventional and modern day amalgams, it has been found that the surfaces of the components of conventional amalgam carriers which come into contact with such amalgams become severely abraded during use and consequently tend to wear at a fast rate.

More particularly, as noted above, the amalgam is condensed or packed into the sleeve recess or cavity prior to its being dispensed whereupon the plunger is moved forwardly to introduce amalgam into the tooth cavity. However, a small amount of the amalgam tends to remain within the sleeve in the clearance space between the plunger and sleeve which abrades the surface of the plunger and sleeve, causing undersirable striations to be formed in these surfaces during use. With continued usage of the instrument, these surfaces are further abraded and the clearance space between the plunger and bore surface unavoidably increases to a point where the instrument becomes unusable. For example, as the clearance between the plunger and internal bore surface increases, the possibility of the plunger binding within the sleeve increases, and, further, when the plunger is actuated to expel the amalgam, increasing amounts of the latter tend to remain within the sleeve in the continuously enlarging clearance space between the plunger and sleeve. For these reasons, conventional amalgam carriers and dispensers must be periodically replaced at relatively short intervals.

Attempts have been made to overcome the problems discussed above. For example, in U.S. Pat. No. 2,903,794, an amalgam carrier is illustrated comprising a plunger disposed within a sleeve, the plunger comprising an outer portion and an inner portion formed of a flexible material, such as Teflon. However, these attempts have not alleviated the problem. Such instruments are also not acceptable since their tactile feel is quite different from that to which dentists are normally accustomed. Further, attempts have been made to overcome the problem by reducing the clearance between the plunger and sleeve. It has been found that these attempts, rather than alleviating the problem, have aggravated the same by increasing the abrasion.

SUMMARY OF THE INVENTION

Accordingly, one object of the present invention is to provide a new and improved amalgam carrier and dispenser whose useful life is significantly greater than that of conventional instruments.

Another object of the present invention is to provide a new and improved amalgam carrier and dispenser wherein the rate and extent of abrasion of the component surfaces caused by the amalgam during use is significantly reduced.

Still another object of the present invention is to provide a new and improved amalgam carrier and dispenser having an increased life relative to conventional instruments and which retains the tactile sense and balance to which dentists are normally accustomed.

Briefly, in accordance with the present invention, these and other objects are obtained by providing an amalgam carrier and dispenser including an open ended sleeve element having a substantially rectilinearly extending internal bore terminating at a free end and a plunger element having a substantially rectilinearly extending plunger portion, the latter having a forward end region and a terminal end region. The terminal end region of the plunger portion has an axial length which terminates at a free end surface. The plunger portion is located within the bore of a sleeve element such that the plunger element is axially slideable therewithin. Means are associated with the sleeve element for axially moving the plunger portion within the sleeve element bore between a first position wherein the free end surface of the plunger portion is located interiorly of the sleeve element bore recessed inwardly from the free end of the sleeve element a predetermined distance thereby defining a cavity within the sleeve element for carrying amalgam and a second position wherein at least a portion of the axial length of the terminal end region of the plunger portion extends exteriorly of the sleeve element bore. The structure described above is conventional.

According to the invention, the terminal end region of the plunger portion is formed of a wear resistant material having a hardness which is greater than the hardness of the type of stainless steel conventionally utilized in amalgam carriers, i.e., about 20 on the Rockwell "C" scale and, preferably, has a hardness of at least about 45 on the Rockwell "C" scale. In the illustrated embodiments, the terminal end region of the plunger portion comprises a tip portion which is affixed to the forward end region of the plunger portion, such as by silver soldering or welding. Means for accurately locating the tip portion with respect to the forward end region of the plunger portion are provided. For example, a pin joint or cone joint may be utilized so that the tip portion formed of the hardened material is precisely located relative to the forward end region of the plunger portion. The tip portion is preferably formed of a hard steel material such, for example, as a carbide steel.

Additionally, according to the invention, the clearance between the plunger portion and the internal bore of the sleeve element is reduced relative to that of conventional instruments. Thus, the clearance between the outer surface of the plunger portion and the internal bore of the sleeve element is less than about 0.0025 inches and, preferably, is about 0.0010 inches. In this connection, it has been found that although the beneficial effects of the invention are obtained solely through the provision of the hard terminal end region for the plunger portion, the effective life is even further increased through the reduction of the clearance as recited above. This is entirely unexpected since, as noted above, when such clearances have been reduced in the past, the abrasion effects have in fact not been reduced but in some cases have been increased. More particularly, when the plunger portion is provided with a hardened tip region and conventional clearances are maintained, it has been found that since the plunger tip region resists abrasion due to the hardness of the material from which it is formed, the amalgam located in the clearance area will be urged against the sleeve bore surface with a somewhat greater force than otherwise and, therefore, the sleeve bore is abraded to a somewhat greater extent than that which normally occurs in the use of conventional instruments. By reducing the clearance, a greater amount of amalgam is expelled from the sleeve recess during operation and, consequently, the abrasion of not only the tip region of the plunger portion is reduced, but, additionally, the sleeve bore will not be subject to the undue abrasion which would otherwise occur where the tip region is formed of a hard material and where conventional clearances are maintained.

Further, it has been found desirable to provide the axial length of the terminal end region of the plunger portion to be greater than a certain minimum value. Thus, the axial length should be greater than about 0.01 inches and, preferably, greater than about 0.06 inches. In this connection, it has been found that by providing the hardened terminal region with these particular axial length dimensions, the amalgam will not adversely affect the regions adjacent to the forward end region of the plunger portion which itself is formed of a softer material, such as stainless steel, until the useful life of the instrument has expired.

DESCRIPTION OF THE DRAWINGS

A more complete appreciation of the present invention and many of the attendant advantages thereof will be readily appreciated as the same becomes better understood by reference to the following detailed description when considered in connection with the accompanying drawings in which:

FIGS. 1a-c are partial side elevation views of a conventional amalgam carrier and dispenser illustrating the sequence of operations whereby amalgam carried thereby is dispensed;

FIG. 2 is a side elevation view in partial section illustrating the amalgam carrier and dispenser of the present invention;

FIG. 3 is an enlarged view of one embodiment of the plunger element for use in connection with the present invention, taken partly in section;

FIG. 4 is a fragmentary view taken partly in section of the plunger portion of the present invention illustrating one embodiment for connecting the tip portion thereto;

FIG. 5 is a view similar to FIG. 4 illustrating another embodiment for connecting the tip portion to the plunger portion; and FIG. 6 is an enlarged section view taken along line 6—6 of FIG. 2.

DESCRIPTION OF THE PREFERRED EMBODIMENT

Referring now to the drawings wherein like reference characters designate identical or corresponding parts throughout the several views, FIGS. 1a-1c illustrate the sequence of operations whereby a conventional amalgam carrier and dispenser dispenses amalgam into a tooth cavity. More particularly, a plunger 10 is located within the bore 12 of a sleeve 14 so as to be axially slideable therewithin. As seen in FIG. 1a, plunger 10 is normally located entirely within sleeve 14 so that its end surface 16 is recessed inwardly of the free end 18 of sleeve 14. The dental amalgam 20 is condensed or packed within the bore 12 in the area forwardly of plunger 10 as shown. The dental amalgam is usually an alloy of mercury with one or more of tin, cadmium, silver, and copper.

Turning to FIG. 1b, the amalgam is dispensed by causing the plunger 10 to move forwardly within bore 12 of sleeve 14 until the terminal end region 22 of plunger 10 extends forwardly of the end 18 of sleeve 14 thereby expelling the amalgam 20 from the bore 12. However, as schematically illustrated in FIG. 1b, a small amount of amalgam 20 tends to remain in the clearance space between the plunger and the sleeve bore, this conventional clearance being on the order of about 0.0025 inches.

After the amalgam is dispensed, plunger 10 is retracted into the bore 12 of sleeve 14 as shown in FIG. 1c. During this operation, the amalgam 20 located in the clearance space is rubbed against the plunger and sleeve bore and abrades the surfaces thereof as described above. The amalgam also tends to move upwardly in the bore during continued usage. The extent of the abrasion progressively advances with continued use of the instrument until the plunger either binds in the bore 12 of sleeve 14 or until the clearance between the plunger and bore 12 becomes so large that the instrument no longer functions properly.

The present invention solves the problem described above in a manner which results in the useful life of the amalgam carrier being extended to at least about five times that of conventional instruments. Thus, referring to FIG. 2, one embodiment of an amalgam carrier and dispenser which incorporates the present invention is illustrated. This amalgam carrier and dispenser will be recognized as having the same general configuration as that disclosed in U.S. Pat. No. 1,797,866 to Ivory. The amalgam carrier and dispenser, generally designated 26, comprises a handle member 28 having a reduced diameter forward portion 30 and a cylindrical extension 32. A flat spring 34 is attached at its rearward end to the cylindrical extension 32 by means of clip portion 36. A plunger element 38 has its rearward end fixed within the cylindrical extension 32 and extends forwardly and is deflected upwardly as at 40 to a curved portion 42 and then deflected downwardly to define a plunger portion 44 whose terminal end region 46 serves to expel the amalgam. The rearward end of spring 34 is fixed in position by a set screw 48 which also serves to fix the plunger element 38. The forward end of spring 34 is provided with a downwardly directed lip 50 which engages the rear edge of a slot formed in a forward portion of a lever member 52 which is defined by a rear finger member 54 and a forward portion 56 having downwardly directed side walls which engage the plunger element 38. A sleeve element 58 comprises a short tubular member whose upper end is affixed to the slot formed in the lever member by means of a pair of adjacent flanges 60, 62. In operation, the lower end of the sleeve element is filled with amalgam. Upon depressing the finger member 54 of lever member 52, the lever member is rocked to thereby raise the sleeve element 58 upwardly with respect to the plunger portion 44 located therewithin whereupon the amalgam carried within the bore of sleeve element 48 is expelled. The amalgam, now within the cavity of the tooth, may be packed by the operator by maintaining the finger member 54 depressed in order to keep the terminal end region of the plunger portion protruding beyond the end of the sleeve element.

The plunger element 38 which comprises a component of the amalgam carrier and dispenser 26 is illustrated in FIG. 3. Thus, the plunger element 38 comprises an elongated stem portion 60 having a flat 62 formed at one end into which the shank of the set screw 48 extends to fix the plunger element 38 in place as described above. The forward end of stem portion 60 is deflected upwardly at 40 to define a curved portion 42 and a rectilinearly extending plunger portion 44. The plunger element 38 is preferably formed of conventional materials utilized for such components, such for example as stainless steel.

According to the present invention, the terminal end region 46 of plunger portion 44 is formed of a wear resistant material which has a hardness greater than the hardness of the type of stainless steel conventionally utilized in amalgam carriers, namely, about 20 on the Rockwell "C" scale. More particularly, it has been found that by forming the terminal end region 46 of plunger portion 44 of material whose hardness is preferably about 45 or greater on the Rockwell "C" scale, the abrasion of the plunger portion of the amalgam carrier and dispenser is significantly reduced thereby unexpectedly increasing the expected life of the instrument from five to ten times that of conventional instruments.

It is understood that the plunger element may be metallurgically treated so that its terminal end region is hardened to achieve the advantages described above. However, according to the preferred embodiment of the invention, the terminal end region of the plunger portion preferably comprises an axially extending tip portion 64 having a pair of transverse end surfaces 66, 68, the end surface 66 comprising the free end surface of the plunger portion. The other end surface 68 is integrally affixed to the terminal connecting end surface 70 of the forward end region 72 of the plunger portion 44. Thus, the connecting end surfaces 68, 70 of tip portion 64 and forward end region 72 can be integrally affixed by any conventional means such, for example, as by conventional silver soldering techniques or by welding.

As noted above, the tip portion 64 is formed of a material whose hardness preferably is at least equal to or greater than 45 on the Rockwell "C" scale. For example, a carbide steel material may be advantageously utilized. Further, tungsten carbide has been found especially suitable.

It will be understood that when the present invention is practiced utilizing a tip portion of the type described above, the accurate positioning thereof on the connecting surface 70 of the forward end region 72 of plunger portion 44 is essential. To this end, means for accurately locating the tip portion 64 on the end of the plunger portion 44 are illustrated in FIGS. 4 and 5. Referring to FIG. 4, a "pin joint" is illustrated wherein a pin 74 axially extends from the connecting surface 68 of tip portion 64 and is received in an aligned bore formed in the plunger portion forward end region 72. By forming the pin and bore precisely on the longitudinal axis of the pin portion 64 and forward end region 72 of plunger 44, an accurate location of the tip portion with respect to the forward end region of the plunger portion is achieved. Alternatively, the "cone joint" illustrated in FIG. 5 can be utilized wherein the connecting surface 68 of the tip portion 64 is formed having a conical protruding configuration while the connecting surface 70 of the forward region 72 of plunger portion 44 is formed having a conical recessed configuration which corresponds to the protruding conical configuration. By forming these conical configurations with an axis which is aligned with the longitudinal axis of the plunger portion 44, an accurate location of the tip portion on the forward end region of plunger portion 44 is facilitated.

According to another feature of the present invention, the clearance between at least the terminal end region of the plunger portion 44 and the bore of the sleeve element 58 is preferably maintained below a certain value. More particularly, referring to FIG. 6, the clearance space 74 is preferably less than about 0.0025 inches. This provision has been found to alleviate the problem of increased erosion of the sleeve bore which would otherwise occur due to the increased resistance to abrasion of the plunger terminal end region and the consequent increase in force with which the amalgam is urged against the sleeve bore. It has been found preferably to provide a clearance of about 0.001 inches. However, clearances as small as 0.00025 inches have worked satisfactorily.

Further, the axial length of the tip portion 64 should advantageously be greater than 0.06 inches although reduction in abrasion can be achieved using a tip portion whose axial length is at least about 0.01 inches.

Thus, in one preferred embodiment, the diameter of the terminal end region of the plunger portion, designated A in FIG. 6, is about 0.081 inches, the diameter of the bore of the sleeve element, designated B, is about 0.0815 inches and the axial length of the tip portion 64, designated C, is about 0.062 inches.

Thus, according to the present invention, a simple and inexpensive modification of conventional amalgam carriers and dispensers provides an unexpected significant increase in the expected life of such instruments heretofore not attainable.

Obviously, numerous modifications and variations of the present invention are possible in the light of the above teachings. It is therefore to be understood that within the scope of the claims, the invention may be practiced otherwise than specifically described herein.

What is claimed is:

1. An amalgam carrier and dispenser comprising:
a handle;

a plunger element affixed to said handle, said plunger element having a substantially rectilinearly extending portion having a forward end region and a terminal end region, the latter having an axial length which terminates at a free end surface;

an open ended sleeve element having a substantially rectilinearly extending internal bore terminating at a free end, said plunger portion of said plunger element being located within said bore such that said plunger element is axially slideable within said sleeve element bore;

lever means associated with said sleeve element for axially moving said plunger portion within said sleeve element bore between a first position wherein said free end surface of said plunger portion is located interiorly of said sleeve element bore recessed inwardly from said free end of said sleeve element a predetermined distance so as to define a cavity within said sleeve element for carrying amalgam and a second position wherein at least a portion of the axial length of said terminal end region of said plunger portion extends exteriorly of said sleeve element bore so that said free end surface of said plunger portion extends beyond said free end of said element to dispense the amalgam carried in the cavity; and wherein said terminal end region of said plunger portion is formed of wear resistant material which has a hardness greater than about 20 on the Rockwell C scale.

2. An amalgam carrier and dispenser as recited in claim 1 wherein the hardness of said terminal end region of said plunger portion is greater than about 45 on the Rockwell C scale.

3. An amalgam carrier and dispenser as recited in claim 2 wherein the clearance between the outer surface of said plunger portion and said internal bore of said sleeve element is less than about 0.0025 inches.

4. An amalgam carrier and dispenser as recited in claim 3 wherein said clearance is about 0.001 inches.

5. An amalgam carrier and dispenser as recited in claim 3 wherein said terminal end region of said plunger portion comprises an axially extending tip portion having a pair of transverse end surfaces one of which comprises said free end surface and the other of which comprises a connecting end surface, said tip portion being integrally affixed to a connecting end surface of said forward end region of said plunger portion.

6. An amalgam carrier and dispenser as recited in claim 5 wherein said tip portion is silver soldered to said plunger portion forward end region.

7. An amalgam carrier and dispenser as recited in claim 5 wherein said tip portion is welded to said plunger portion forward end region.

8. An amalgam carrier and dispenser as recited in claim 5 wherein one of said connecting surfaces of said tip portion and said plunger portion forward end region has a pin axially extending therefrom and the other of said tip and plunger portions has a bore formed therein which opens into the respective connecting surface thereof and which is axially aligned with said pin so that said bore is adapted to receive said pin to facilitate an accurate location of said tip portion with respect to said forward end region of said plunger portion.

9. An amalgam carrier and dispenser as recited in claim 5 wherein one of said connecting surface of said tip portion and said plunger portion forward end region is formed having a conical protruding configuration and the other of said connecting surfaces is formed having a conical recessed configuration which corresponds to said protruding conical configuration so that said conical recess is adpated to receive said pin to facilitate an accurate location of said tip portion.

10. An amalgam carrier and dispenser as recited in claim 3 wherein said wear resistant material comprises a carbide steel material.

11. An amalgam carrier and dispenser as recited in claim 3 wherein said wear resistant material comprises tungsten carbide.

12. An amalgam carrier and dispenser as recited in claim 3 wherein said axial length of said terminal end region of said plunger portion is at least about 0.01 inches.

13. An amalgam carrier and dispenser as recited in claim 12 wherein said axial length is at least about 0.06 inches.

* * * * *